United States Patent
Slaughter et al.

(10) Patent No.: US 10,488,309 B2
(45) Date of Patent: Nov. 26, 2019

(54) TEST SPECIMEN AND METHOD OF FORMING AND TESTING THE TEST SPECIMEN

(71) Applicant: The Boeing Company, Chicago, IL (US)

(72) Inventors: Victor Blakemore Slaughter, St. Louis, MO (US); Rigoberto Perez, Chesterfield, MO (US)

(73) Assignee: The Boeing Company, Chicago, IL (US)

(*) Notice: Subject to any disclaimer, the term of this patent is extended or adjusted under 35 U.S.C. 154(b) by 97 days.

(21) Appl. No.: 15/616,286

(22) Filed: Jun. 7, 2017

(65) Prior Publication Data
US 2018/0356322 A1 Dec. 13, 2018

(51) Int. Cl.
*G01N 3/02* (2006.01)
*G01N 3/28* (2006.01)
*G01N 3/62* (2006.01)
*G01N 3/08* (2006.01)

(52) U.S. Cl.
CPC .................. *G01N 3/02* (2013.01); *G01N 3/08* (2013.01); *G01N 3/28* (2013.01); *G01N 3/62* (2013.01)

(58) Field of Classification Search
CPC .. G01N 3/02; G01N 3/08; G01N 3/28; G01N 3/62
USPC .......................................................... 73/804
See application file for complete search history.

(56) References Cited

U.S. PATENT DOCUMENTS

| 5,528,942 A * | 6/1996 | Baratta | ..................... G01N 3/02 |
| | | | 73/818 |
| 5,913,246 A * | 6/1999 | Simonelli | ................ G01N 3/34 |
| | | | 73/794 |
| 7,360,442 B2 | 4/2008 | Broadley et al. | |
| 2006/0159614 A1* | 7/2006 | Apelqvist | ................ G01N 3/08 |
| | | | 423/659 |
| 2010/0145469 A1* | 6/2010 | Barralet | .............. A61F 2/30767 |
| | | | 623/23.56 |
| 2017/0322129 A1* | 11/2017 | Wenski | ................... G01N 3/068 |

OTHER PUBLICATIONS

Bayoumi et al. "Effect of Surface Finish on Fatigue Strength", En. Frac. Mech. vol. 51, No. 5, pp. 861-870 (Year: 1995).*
American Society for Testing and Materials, ASTM E8 / E8M-16a, "Standard Test Methods for Tension Testing of Metallic Materials", ASTM International, West Conshohocken, PA, 2016.
Fatemi et al., "Multiaxial Fatigue Behavior of Additive Manufactured TI-6AL-4V", 17$^{th}$ International ASTM/ESIS Symposium on Fatigue and Fracture Mechanics (41$^{st}$ National Symposium on Fatigue and Fracture Mechanics), May 10-12, 2017, Toronto, ON Cananda.

* cited by examiner

*Primary Examiner* — Nathaniel T Woodward
(74) *Attorney, Agent, or Firm* — Walters & Wasylyna LLC (57) ABSTRACT

A test specimen is provided. The test specimen includes a coupon. The coupon includes a test portion and grip portions. The grip portions are located on opposite axial ends of the coupon. The test portion is located between the grip portions. The coupon further includes a void extending into the coupon from at least one of the axial ends. The void is defined by a wall having a surface thickness at the test portion that corresponds to a predetermined surface thickness of interest. The coupon is configured to be secured to a test machine for conducting load tests on the coupon.

20 Claims, 6 Drawing Sheets

TEST SPECIMEN AND METHOD OF FORMING AND TESTING THE TEST SPECIMEN

FIELD

This application relates to a test specimen and method of making and testing the test specimen.

BACKGROUND

The strength and fatigue properties of a material are crucial in component and part design, particularly in the aerospace industry. Typically, this information is found through load testing a sample of the material and observing its behavior under various load conditions. For example, a sample of material or test specimen may be loaded with a tensile load and/or a compressive load and tested until failure occurs.

Solid round bar coupons have been used as test specimens. However, a round bar coupon may not represent thin wall material properties accurately. An analyst would have to determine the applicability of the measurement to the geometry of the component, which may not be ideal. Also, surface finishes affect material properties and the thinner the material, the more its properties can be affected by the surface finish. Because of this effect, standard material property test methods such as ASTM E8, ASTM E606, ISO 1143, and ASTM E466 are not suitable for correlating or quantifying surface finish effects with material thickness when dealing with coupons having thin walls.

Utilizing a flat coupon would be another approach for material tests, but edge effects can make the results highly inaccurate. For example, the edge of the cross section can complicate test results for additive manufactured coupons that have a rough surface.

SUMMARY

In one embodiment, a test specimen is provided. The test specimen includes a coupon. The coupon includes a test portion and grip portions. The grip portions are located on opposite axial ends of the coupon. The test portion is located between the grip portions. The coupon further includes a void extending into the coupon from at least one of the axial ends. The void is defined by a wall having a surface thickness at the test portion that corresponds to a predetermined surface thickness of interest. The coupon is configured to be secured to a test machine for conducting load tests on the coupon.

In another embodiment, an apparatus is provided. The apparatus includes a test specimen. The test specimen includes a coupon. The coupon further includes a void extending into the coupon from a first axial end of the coupon. The void is defined by a wall having a surface thickness at the test portion that corresponds to a predetermined surface thickness of interest. The apparatus further includes a test machine. The coupon is secured to the test machine, and the test machine conducts load tests on the coupon.

In another embodiment, a method is provided. The method includes making a test specimen. The test specimen includes a coupon, wherein making the test specimen includes making a void into the coupon that extends from a first axial end of the coupon. The void is defined by a wall having a surface thickness that corresponds to a predetermined surface thickness of interest. The method further includes securing the coupon to a test machine and conducting load tests on the coupon using the test machine.

Other embodiments of the disclosed a test specimen and method of making and testing the test specimen will become apparent from the following detailed description, the accompanying drawings and the appended claims.

DETAILED DESCRIPTION

Figure 1:
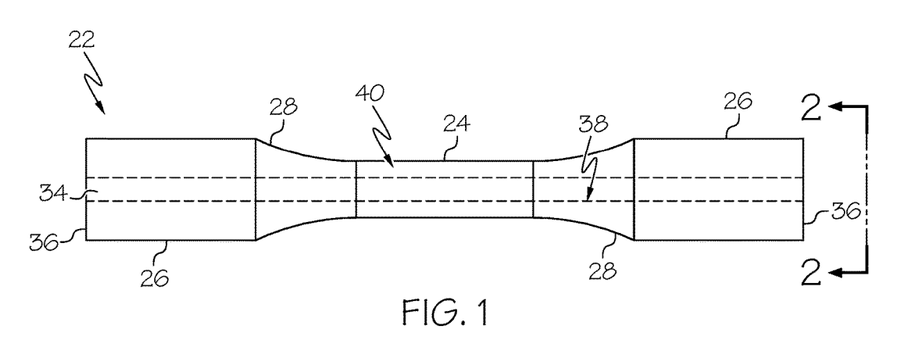
FIG. 1 is a side view of a coupon of a test specimen according to an embodiment.
Figure 2:
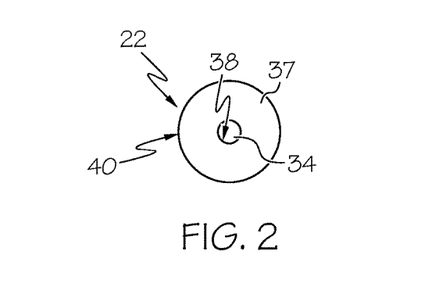
FIG. 2 is a view taken along line 2-2 of FIG. 1.
Figure 3:
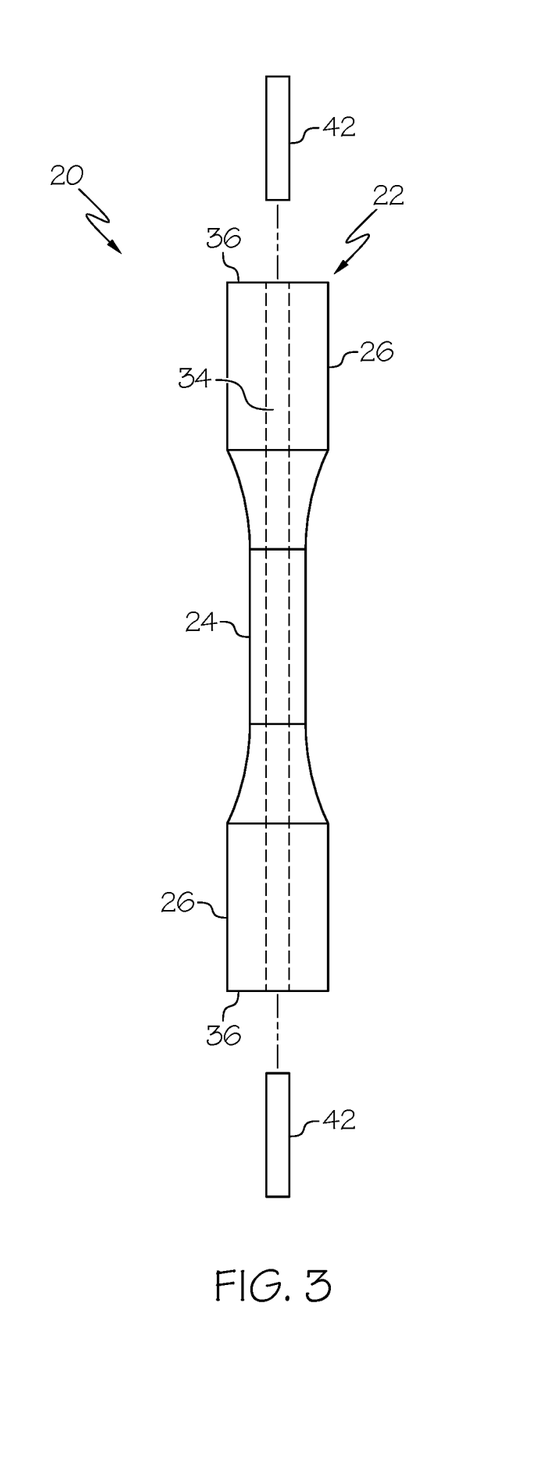
FIG. 3 is an exploded view of the test specimen.
Figure 4:
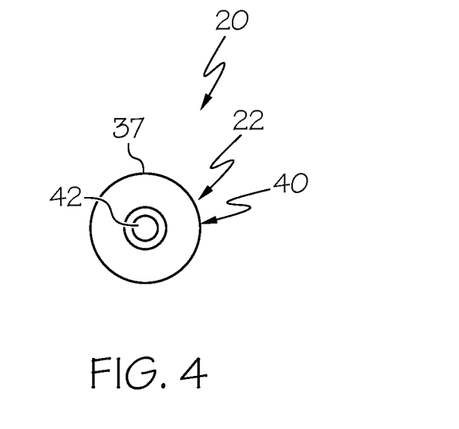
FIG. 4 is an end view of the test specimen.

FIGS. 3 and 4 show a test specimen 20. The test specimen 20 is a relative surface finish test specimen. The test specimen 20 includes a coupon 22. Referring to FIGS. 1 and 2, the coupon 22 is generally cylindrical in shape and comprises a cylindrical test portion 24 located between two cylindrical grip portions 26, which are located on opposite axial ends 36 of the coupon 22. The test portion 24 has a smaller diameter than the grip portions 26 and concavely curves radially outwardly toward each grip portion 26 at each of the junctions 28 of each grip portion 26. The grip portions 26 are designed to transfer loads smoothly into the test portion 24 without producing local stress concentrations. The grip portions 26 have a larger diameter than that of the test potion 24 so that if slight concentrations of stress are present these will be directed to the test portion, and failures will occur only where measurements are being taken. The grip portions 26 are configured to be gripped and held by, for example, holders or grips 30 (FIG. 5) of a test machine 32 for testing the coupon in accordance with material property test methods such as ASTM E8, ASTM E606, ISO 1143, and ASTM E466.

The coupon 22 is generally hollow with a central cylindrical through passage or void 34 extending longitudinally from one axial end 36 to the other axial end 36 of the coupon. This configuration provides for a continuous thin circular wall 37 of the coupon 22 that defines the void 34. The wall 37 has desired roughness on interior and exterior surfaces 38, 40 and a thickness at the test portion 24 that corresponds to a predetermined thickness of interest. The predetermined thickness of interest may be the thickness of the actual component being used. The grip portions 26 are pre-drilled. The coupon 22 generally comprises a sample material formed in one piece. The material may be a metal or other material(s) such as a plastic material. Alternatively, the passage or void 34 may extend into the coupon 22 from one of the axial ends 36 and not extend through the other axial end 36.

Referring to FIGS. 3 and 4, the test specimen 20 may optionally include a pair of cylindrical end plugs 42. One end plug 42 extends into the void 34 at one axial end 36 and another end plug 42 extends into the void 34 at the other opposite axial end 36. The diameter of each end plug 42 is similar to the diameter of the passage or void 34 such that the end plugs 42 sufficiently seal the void 34. The end plugs 42 plug or seal the void 34 to prevent chemicals or abrasive media used to smooth the exterior surface 40 of the wall from entering the void 34 and altering the interior surface 38 of the wall 37. The optional end plugs 42 also provide support to the grip portions 26 to help prevent the collapse of the hollow grip portions 26 under the gripping force applied by the holders or grips 30 of the test machine 32. The end plugs 42 have generally smooth surfaces to allow them to slide into the void 34. Sealant may be provided between the end plugs 42 and the interior surface 38 of the wall 37 to further seal the void 34. Alternatively, the end plugs may be comprised of threaded inserts that threadily engage a threaded portion of the interior surface of the wall.

Figure 5:
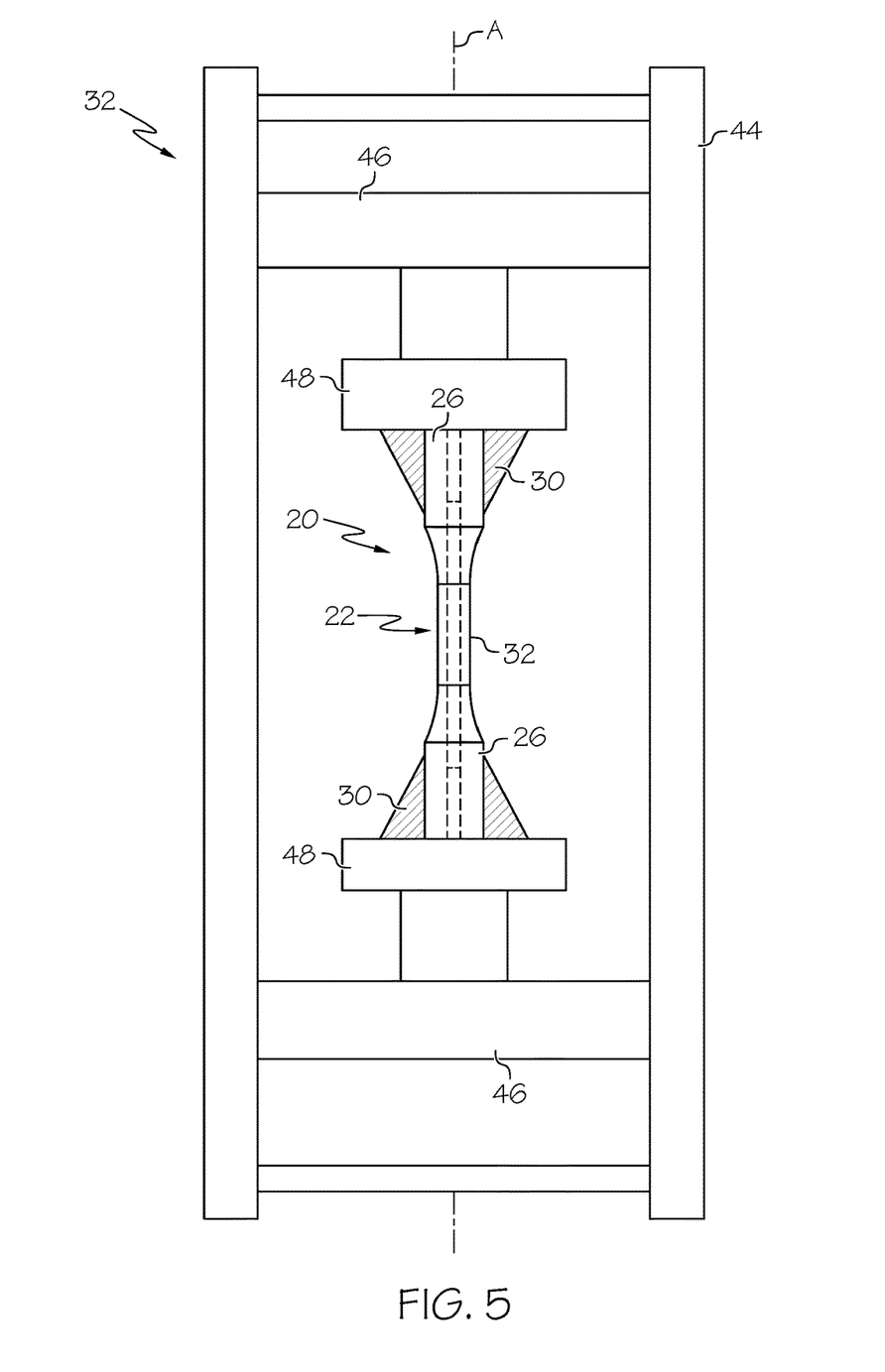
FIG. 5 is a side view a test machine with the test specimen of FIGS. 3 and 4.

As seen in FIG. 5, the test specimen 20 is secured to the test machine 32 for testing. Specifically, the exemplary test machine 32 includes the holders 30 that grip the grip portions 26 of the coupon 22. The test machine 32 may also include a test frame 44, at least one load assembly 46, and a pair of load balancing assemblies 48. The pair of load balancing assemblies 48 may securely retain the coupon 22 via the holders 30 at two opposing ends. Each of the load balancing assemblies 48 may be suitably sized to grip and retain a correspondingly sized coupon 22. The load assembly 46 may deliver a load (e.g., tensile or compression load) to the coupon 22 by moving at least one of the load balancing assemblies 48 along a single axis A. The test methods may include ASTM E8, ASTM E606, ISO 1143, and ASTM E466 test methods.

ASTM E8 test methods cover the tension testing of metallic materials in any form at room temperature. This test determines important mechanical properties such as yield strength, ultimate tensile strength, elongation, and reduction of area. ASTM E8 tensile tests determine the ductility and strength of various metals when the materials undergo uniaxial tensile stresses. Such information is important for alloy development, design, quality control, and comparison of different sets of metals. ASTM E466 test methods cover axial fatigue tests of metallic materials. This test determines the fatigue strength by testing metallic test specimens at various constant amplitude cyclic stress levels. Each test continues until failure of the specimen occurs or until a certain number of stress cycles is applied. It should be contemplated that the test specimen 20 may be secured to other types of test machines and may include testing methods other than ASTM E8 and ASTM E606 such as ISO 1143 and ASTM E466 test methods as well. It should be contemplated that the coupon may have any geometric shape other than cylindrical and dimensions other than the above-mentioned dimensions.

Figure 7:
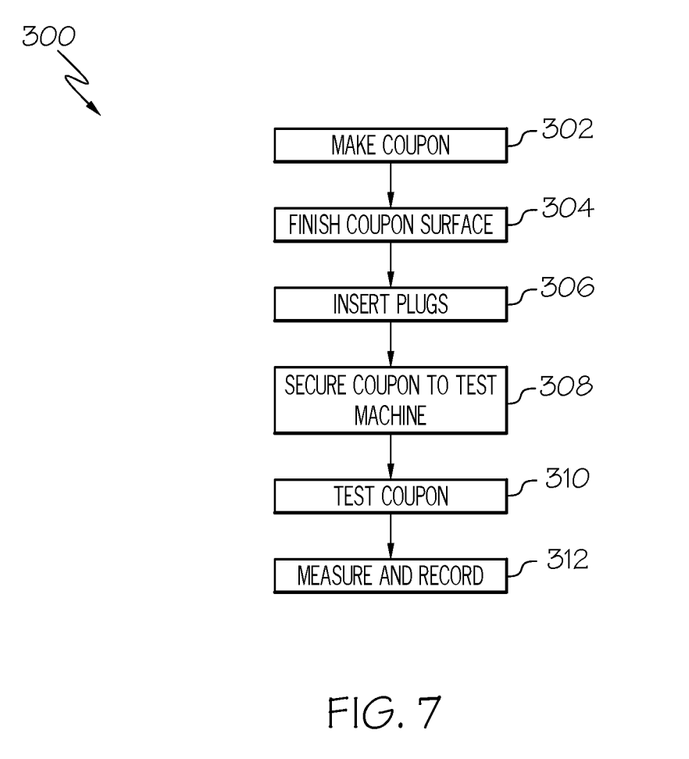
FIG. 7 is flow diagram of the method of making and testing the test specimen of FIGS. 3 and 4.

FIG. 7 illustrates a method 300 for making and testing a test specimen 20. In step 302, the coupon 22 is made. The coupon 22 may be made by an additive manufacturing or 3D printing process in which layers of material are formed or deposited under computer control. The additive manufacturing processes for metal sintering or melting (such as selective laser sintering, direct metal laser sintering, and selective laser melting) may be utilized. Alternatively, the coupon 22 may be made by other suitable manufacturing processes such as die casting, fabrication, stamping, and machining. The void 34 may be made by a suitable process such as pre-drilled, deposition or alternatively made during the manufacturing process. Although the coupon 22 is shown to be cylindrical in shape, the coupon 22 can be any other shape. The coupon 22 may include any number of laminate layers at any lay-up angle. The process for making the coupon 22 may also be automated, such as by machine or robot, to increase the speed of coupon fabrication.

In step 304, the interior and exterior surfaces 38, 40 of the coupon are finished. The surface finishing options for the grip portions 26 may include machined, as deposited (no surface finishing), and modified surface. The surface finishing options for the test portion 24 are machined, as deposited, and modified surface. The modified surface may a surface that is intentionally roughened. The interior and exterior surfaces 38, 40 may have different surface finishes to assess the combined surface impact on strength and fatigue life characteristics. The surfaces may also have a highly polished finish.

In step 306, the optional end plugs 42 are inserted into the void 34 at the axial ends 36 of the coupon 22 to seal the void 34. In step 308, the coupon 22 is then secured and fixed to the load balancing assemblies 48 of the test machine 32. This step may include gripping the grip portions 26 of the coupon 22 by the holders 30 of the test machine 32. The step of securing the coupon 22 to the load balancing assemblies 48 may be automated, such as by machine or robot, to increase the speed of insertion of the coupon 22. The coupon 22 may be attached to this or other testing machines by a combination of four methods: secured from the outside, expansion from the inside, threading on the outside, and threading on the inside.

In step 310, load tests may then be performed on the test portion 24 of the test specimen 20. In step 312, the test machine 32 may measure and record the results of the test performed in step 310. These tests may include static tests. For example, in a static tension test, the test machine 32 uniformly stretches the test portion 24 of the coupon 22. The length of the test portion 24 is then measured at different loads. These measurements are used to compute strain. Static compression tests may also be performed by the test machine 32 to determine a material's response to crushing, or support-type loading. Static shear and bending tests may also be administered on the coupon 22 to indicate the deformation response of a material to forces applied tangentially to the coupon 22. The static test may include pulling or compressing the axial ends 36 of the coupon 22 until the coupon 22 breaks.

The tests may also include fatigue tests to test the behavior of materials under fluctuating loads. Fatigue testing may be used to determine how many load cycles the coupon 22 can sustain or the failure load level for a given number of cycles. For example, a specified mean load and an alternating load may be applied to the coupon 22 and the number of cycles required to produce failure (fatigue life) is recorded. Fatigue testing may involve loading and unloading axial forces (pulling and/or pushing) on the coupon 22 for a number of cycles until the coupon fails. The fatigue test may include cycles of bending and relaxing the coupon 22 on a different test machine until the coupon 22 fails. The fatigue test may include placing the coupon 22 in chucks. The alignment of these chucks induce cyclic tension and compression loads in the coupon when rotated. The coupon 22 is rotated for a number of cycles until the coupon 22 fails or a determined number of cycles are reached. The testing step 310 may include ASTM E8 test methods or other suitable test methods such as ASTM E606, ISO 1143, and ASTM E466.

In one exemplary test, a load may be applied to the coupon 22. The load may be applied by linearly moving at least one load balancing assembly 48 along an axis of movement A with respect to an opposed load balancing assembly 48 (FIG. 5). For example, a tensile load may be applied to the coupon 22 by moving the load balancing assemblies 48 away from one another. As another example, a compressive load may be applied by moving the load balancing assemblies 48 toward one another. The process of applying the load to the coupon 22 may be automated, such as by machine or computer controlled control unit.

Figure 6:
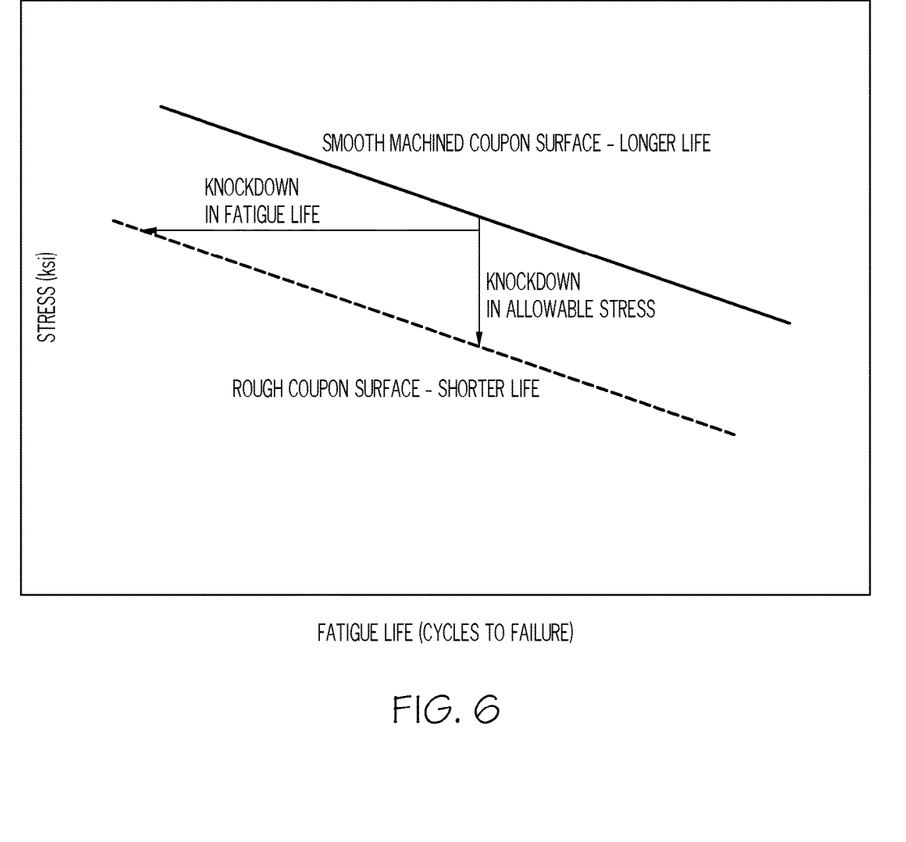
FIG. 6 is a graph of the stress versus the fatigue life for two coupons with different types of surfaces.

Similar tests may be performed on coupons with different surface finishes and then compared. For example, static and fatigue tests may be performed on a group of coupons with manufactured surface finishing. The same tests then may be performed on coupons with a machined surface finish. The tests for each group are then compared to see the relative differences between them. For example, FIG. 6 shows a typical metal fatigue data for coupons with a rough surface and coupons with a smooth machined surface.

For step 312, the behavior of the coupon 22 in response to an applied load may be measured and recorded. A strain gauge may be used to measure and record the load applied during the test. The process of measuring and recording the load applied to the coupon 22 may be automated, such as by a computer.

Figure 8:
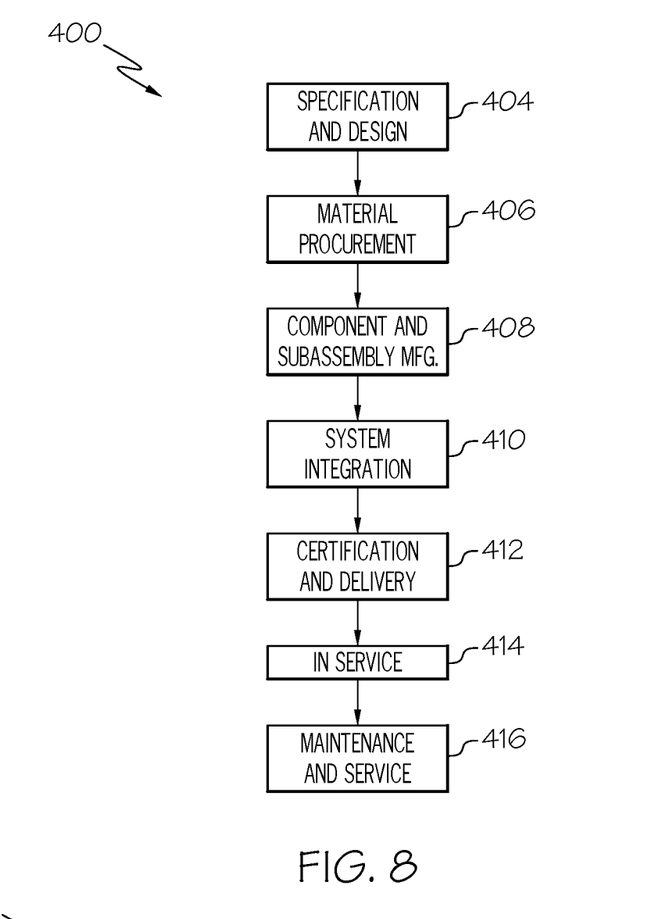
FIG. 8 is flow diagram of an aircraft manufacturing and service methodology.
Figure 9:
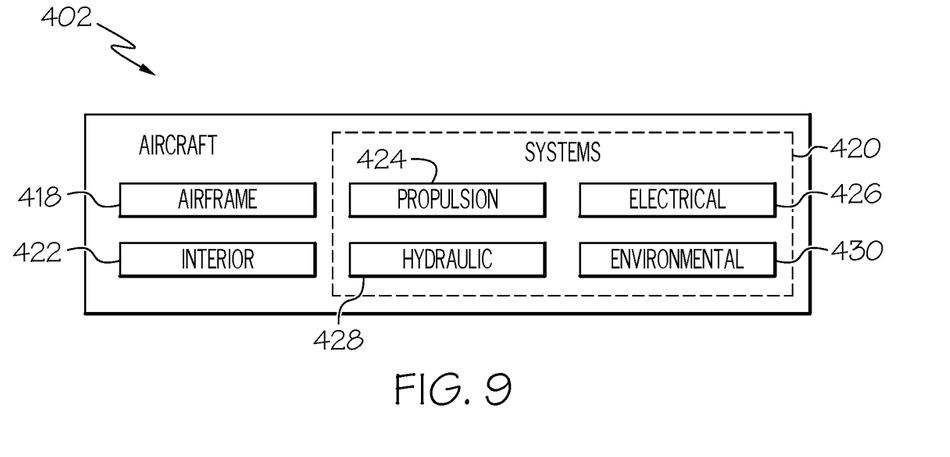
FIG. 9 is a block diagram of an aircraft.

Examples of the disclosure may be described in the context of an aircraft manufacturing and service method 400, as shown in FIG. 8, and an aircraft 402, as shown in FIG. 9. During pre-production, the aircraft manufacturing and service method 400 may include specification and design 404 of the aircraft 402 and material procurement 406. During production, component/subassembly manufacturing 408 and system integration 410 of the aircraft 402 takes place. Thereafter, the aircraft 402 may go through certification and delivery 412 in order to be placed in service 414. While in service by a customer, the aircraft 402 is scheduled for routine maintenance and service 416, which may also include modification, reconfiguration, refurbishment and the like.

Each of the processes of method 400 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, single individual, and so on. The proposed application could be used on many different materials and surface finishes across many industries in addition to the aerospace industry.

As shown in FIG. 9, the aircraft 402 produced by example method 400 may include an airframe 418 with a plurality of systems 420 and an interior 422. Examples of the plurality of systems 420 may include one or more of a propulsion system 424, an electrical system 426, a hydraulic system 428, and an environmental system 430. Any number of other systems may be included.

The test specimen provides a continuous thin walled surface in the test or gauge portion that is free of edge effects during testing. Coupons can be prepared with differing surface finishes to measure the impact and repeatability of the surface finish on mechanical performance. Likewise, coupons of differing wall thickness could shed light on the sensitivity of the structure to surface finish. The proposed application also improves the accuracy of data collected during static and fatigue testing such as ASTM E8 and E466. The use of hollow round bar coupons as test specimens creates a better representation of thin wall surfaces of actual parts without complications of edge effects associated with flat coupons. Also, hollow coupons can be built with different interior and exterior surfaces to assess the relative surface impact on material strength and fatigue life characteristics. Various surface conditions and wall thicknesses allow for relative characterization of the impact of surface finishes on mechanical performance. This configuration enables accurate testing of thin walled materials, which thus enables one to correlate surface finish effects with material thickness, Although various embodiments of the disclosed test specimen and method of making and testing the test specimen have been shown and described, modifications may occur to those skilled in the art upon reading the specification. The present application includes such modifications and is limited only by the scope of the claims.

What is claimed is:

1. An apparatus comprising:
   a first coupon being a product of additive manufacturing and comprising a first void extending from a first axial end of said first coupon, said first void being defined by a first wall having a first surface thickness, said first coupon further comprising a first surface having a first finish;
   a second coupon being a product of additive manufacturing and being substantially compositionally identical to said first coupon, said second coupon comprising a second void extending from a second axial end of said second coupon, said second void being defined by a second wall having a second surface thickness that is substantially equal to said first surface thickness, said second coupon further comprising a second surface having a second finish that is different from said first finish; and
   a test machine configured to conduct load tests on said first coupon and said second coupon.

2. The apparatus of claim 1 wherein said first coupon and said second coupon are cylindrical.

3. The apparatus of claim 1 wherein:
   said first coupon further comprises first grip portions located at opposite axial ends of said first coupon and a first test portion located between said first grip portions; and
   said second coupon comprises second grip portions located at opposite axial ends of said second coupon and a second test portion located between said second grip portions.

4. The apparatus of claim 3 wherein said test machine comprises:
   a plurality of holders that grip said first grip portions and said second grip portions to secure said first coupon and said second coupon to said test machine;
   a test frame;
   at least one load assembly; and
   a pair of load balancing assemblies that securely retain said first coupon and said second coupon, wherein said load assembly delivers a load to said first coupon and said second coupon by moving at least one of said load balancing assemblies along a single axis.

5. The apparatus of claim 1 wherein the load tests comprise at least one of ASTM E8, ASTM E606, ISO 1143, and ASTM E466 test methods, or any combination of ASTM E8, ASTM E606, ISO 1143, and ASTM E466 test methods.

6. The apparatus of claim 1 wherein the load tests comprise static and fatigue tests.

7. The apparatus of claim 1 wherein said first void is filled with an end plug.

8. A method comprising:
additively manufacturing a first coupon comprising a first void extending from a first axial end of said first coupon, said first void being defined by a first wall having a first surface thickness, said first coupon further comprising a first surface having a first finish;
additively manufacturing a second coupon that is substantially compositionally identical to said first coupon, said second coupon comprising a second void extending from a second axial end of said second coupon, said second void being defined by a second wall having a second surface thickness substantially equal to said first surface thickness, said second coupon further comprising a second surface having a second finish that is different from said first finish;
conducting a first load test on said first coupon to obtain a first load test result;
conducting a second load test on said second coupon to obtain a second load test result; and
comparing said first load test result with said second load test result.

9. The method of claim 8 wherein said first load test and said second load test comprise conducting static and fatigue tests on said first coupon and said second coupon.

10. The method of claim 8 wherein said conducting said first load test comprises using at least one of ASTM E8, ASTM E606, ISO 1143, and ASTM E466 test methods, or any combination of ASTM E8, ASTM E606, ISO 1143, and ASTM E466 test methods.

11. The method of claim 8 wherein said making said first coupon comprises finishing said first surface.

12. The method of claim 8 wherein:
said first coupon comprises first grip portions located at opposite axial ends of said first coupon and a first test portion located between said first grip portions; and
said second coupon comprises second grip portions located at opposite axial ends of said second coupon and a second test portion located between said second grip portions.

13. The method of claim 12 wherein said test machine grips said first grip portions and said second grip portions to secure said first coupon and said second coupon to said test machine.

14. The method of claim 8 further comprising ascertaining, based on said comparing, an impact that surface finish has on mechanical performance.

15. The method of claim 8 wherein:
said making of said first coupon comprises forming said first coupon as a single monolithic piece; and
said making of said second coupon comprises forming said second coupon as a single monolithic piece.

16. The method of claim 8 further comprising inserting a first end plug into said first void.

17. The method of claim 8 wherein said first finish is machined.

18. The method of claim 8 wherein said second finish is as deposited by additive manufacturing.

19. The method of claim 8 further comprising intentionally roughening at least one of said first surface and said second surface.

20. The method of claim 8 wherein at least one of said conducting said first load test and said conducting said second load test is automated.

* * * * *